(12) United States Patent
Serhan et al.

(10) Patent No.: US 9,949,769 B2
(45) Date of Patent: Apr. 24, 2018

(54) DYNAMIZED INTERSPINAL IMPLANT

(71) Applicant: DEPUY SYNTHES PRODUCTS, INC., Raynham, MA (US)

(72) Inventors: Hassan Serhan, South Easton, MA (US); Alexander Michel DiNello, Palo Alto, CA (US); William Christianson, Duxbury, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/446,554

(22) Filed: Mar. 1, 2017

(65) Prior Publication Data

US 2017/0172632 A1    Jun. 22, 2017

Related U.S. Application Data

(60) Continuation of application No. 15/149,132, filed on May 8, 2016, now Pat. No. 9,662,149, which is a continuation of application No. 15/149,085, filed on May 7, 2016, now Pat. No. 9,662,148, which is a continuation of application No. 15/148,937, filed on
(Continued)

(51) Int. Cl.
| | |
|---|---|
| *A61F 2/44* | (2006.01) |
| *A61B 17/70* | (2006.01) |
| *A61B 17/56* | (2006.01) |
| *A61B 17/68* | (2006.01) |
| *A61B 17/00* | (2006.01) |
| *A61F 2/48* | (2006.01) |

(52) U.S. Cl.
CPC ...... *A61B 17/7065* (2013.01); *A61B 17/7062* (2013.01); *A61B 17/7068* (2013.01); *A61F 2/4405* (2013.01); *A61B 2017/00075* (2013.01); *A61B 2017/00221* (2013.01); *A61B 2017/00964* (2013.01); *A61B 2017/567* (2013.01); *A61B 2017/681* (2013.01); *A61F 2002/482* (2013.01)

(58) Field of Classification Search
CPC ............ A61B 17/7065; A61B 17/7062; A61B 17/768; A61B 2017/00075; A61B 2017/00221; A61B 2017/00964; A61B 2017/567; A61B 2017/681; A61F 2/4405; A61F 2002/482
USPC ........ 606/246–249; 623/17.11, 17.13, 17.15, 623/17.16
See application file for complete search history.

(56) References Cited

U.S. PATENT DOCUMENTS

| | | | |
|---|---|---|---|
| 3,867,728 A | 2/1975 | Stubstad et al. | |
| 4,349,921 A | 9/1982 | Kuntz | |

(Continued)

FOREIGN PATENT DOCUMENTS

| | | |
|---|---|---|
| CN | 101909548 A | 12/2010 |
| DE | 28 04 936 A1 | 8/1979 |

(Continued)

OTHER PUBLICATIONS

[No Author Listed] Link SB Charite—Intervertebral Prosthesis, Brochure, Waldemar Link GmbH & Co., 1988, 29 pages.

(Continued)

*Primary Examiner* — Pedro Philogene
*Assistant Examiner* — David C Comstock
(74) *Attorney, Agent, or Firm* — Nutter McClennen & Fish LLP

(57) ABSTRACT

An interspinous process having a narrowed distal portion.

16 Claims, 9 Drawing Sheets

Related U.S. Application Data

May 6, 2016, now Pat. No. 9,662,147, which is a continuation of application No. 14/845,687, filed on Sep. 4, 2015, now Pat. No. 9,402,654, which is a continuation of application No. 14/134,090, filed on Dec. 19, 2013, now abandoned, which is a division of application No. 10/793,967, filed on Mar. 6, 2004, now Pat. No. 8,636,802.

(56) References Cited

U.S. PATENT DOCUMENTS

| | | |
|---|---|---|
| 4,714,469 A * | 12/1987 | Kenna ............... A61B 17/1757 606/247 |
| 4,759,766 A | 7/1988 | Buettner-Janz et al. |
| 4,759,769 A | 7/1988 | Hedman et al. |
| 4,863,476 A | 9/1989 | Shepperd |
| 4,871,366 A | 10/1989 | von Recum et al. |
| 4,878,915 A | 11/1989 | Brantigan |
| 4,911,718 A | 3/1990 | Lee et al. |
| 4,946,378 A | 8/1990 | Hirayama et al. |
| 5,002,576 A | 3/1991 | Fuhrmann et al. |
| 5,024,670 A | 6/1991 | Smith et al. |
| 5,030,233 A | 7/1991 | Ducheyne |
| 5,071,437 A | 12/1991 | Steffee |
| 5,123,926 A | 6/1992 | Pisharodi |
| 5,134,477 A | 7/1992 | Knauer et al. |
| 5,290,312 A | 3/1994 | Kojimoto et al. |
| 5,306,308 A | 4/1994 | Gross et al. |
| 5,306,309 A | 4/1994 | Wagner et al. |
| 5,314,477 A | 5/1994 | Marnay |
| 5,344,252 A | 9/1994 | Kakimoto |
| 5,370,697 A | 12/1994 | Baumgartner |
| 5,372,660 A | 12/1994 | Davidson et al. |
| 5,401,269 A | 3/1995 | Buttner-Janz et al. |
| 5,425,773 A | 6/1995 | Boyd et al. |
| 5,458,641 A | 10/1995 | Ramirez Jimenez |
| 5,458,642 A | 10/1995 | Beer et al. |
| 5,458,643 A | 10/1995 | Oka et al. |
| 5,507,816 A | 4/1996 | Bullivant |
| 5,514,180 A | 5/1996 | Heggeness et al. |
| 5,522,899 A | 6/1996 | Michelson |
| 5,527,312 A | 6/1996 | Ray |
| 5,534,029 A | 7/1996 | Shima |
| 5,534,030 A | 7/1996 | Navarro et al. |
| 5,554,191 A | 9/1996 | Lahille |
| 5,556,431 A | 9/1996 | Buttner-Janz |
| 5,562,738 A | 10/1996 | Boyd et al. |
| 5,609,635 A | 3/1997 | Michelson |
| 5,645,596 A | 7/1997 | Kim et al. |
| 5,645,599 A | 7/1997 | Samani |
| 5,653,763 A | 8/1997 | Errico et al. |
| 5,665,122 A | 9/1997 | Kambin |
| 5,674,294 A | 10/1997 | Bainville et al. |
| 5,674,296 A | 10/1997 | Bryan et al. |
| 5,676,701 A | 10/1997 | Yuan et al. |
| 5,683,465 A | 11/1997 | Shinn et al. |
| 5,697,977 A | 12/1997 | Pisharodi |
| 5,702,450 A | 12/1997 | Bisserie et al. |
| 5,716,415 A | 2/1998 | Steffee |
| 5,755,798 A | 5/1998 | Papavero et al. |
| 5,772,661 A | 6/1998 | Michelson |
| 5,782,832 A | 7/1998 | Larsen et al. |
| 5,824,093 A | 10/1998 | Ray et al. |
| 5,824,094 A | 10/1998 | Serhan et al. |
| 5,836,948 A | 11/1998 | Zucherman et al. |
| 5,865,846 A | 2/1999 | Bryan et al. |
| 5,865,848 A | 2/1999 | Baker |
| 5,888,224 A | 3/1999 | Beckers et al. |
| 5,888,226 A | 3/1999 | Rogozinski |
| 5,893,889 A | 4/1999 | Harrington |
| 5,893,890 A | 4/1999 | Pisharodi |
| 5,895,428 A | 4/1999 | Berry |
| 5,976,186 A * | 11/1999 | Bao ..................... A61F 2/441 623/17.16 |
| 5,980,522 A | 11/1999 | Koros et al. |
| 5,989,291 A | 11/1999 | Ralph et al. |
| 6,001,130 A | 12/1999 | Bryan et al. |
| 6,019,792 A | 2/2000 | Cauthen |
| 6,022,350 A | 2/2000 | Ganem |
| 6,039,761 A | 3/2000 | Li et al. |
| 6,039,763 A | 3/2000 | Shelokov |
| 6,045,579 A | 4/2000 | Hochshuler et al. |
| 6,063,121 A | 5/2000 | Xavier et al. |
| 6,068,630 A | 5/2000 | Zucherman et al. |
| 6,087,553 A | 7/2000 | Cohen et al. |
| 6,099,531 A | 8/2000 | Bonutti |
| 6,106,557 A | 8/2000 | Robioneck et al. |
| 6,113,637 A | 9/2000 | Gill et al. |
| 6,113,638 A | 9/2000 | Williams et al. |
| 6,126,689 A | 10/2000 | Brett |
| 6,127,597 A | 10/2000 | Beyar et al. |
| 6,136,031 A | 10/2000 | Middleton |
| 6,139,579 A | 10/2000 | Steffee et al. |
| 6,146,387 A | 11/2000 | Trott et al. |
| 6,146,421 A | 11/2000 | Gordon et al. |
| 6,162,252 A | 12/2000 | Kuras et al. |
| 6,176,882 B1 | 1/2001 | Biedermann et al. |
| 6,179,794 B1 | 1/2001 | Burras |
| 6,179,873 B1 | 1/2001 | Zientek |
| 6,183,517 B1 | 2/2001 | Suddaby |
| 6,197,065 B1 | 3/2001 | Martin et al. |
| 6,296,647 B1 | 10/2001 | Robioneck et al. |
| 6,302,914 B1 | 10/2001 | Michelson |
| 6,332,894 B1 | 12/2001 | Stalcup et al. |
| 6,332,895 B1 | 12/2001 | Suddaby |
| 6,368,350 B1 | 4/2002 | Erickson et al. |
| 6,375,681 B1 | 4/2002 | Truscott |
| 6,387,130 B1 | 5/2002 | Stone et al. |
| 6,395,032 B1 | 5/2002 | Gauchet |
| 6,409,766 B1 | 6/2002 | Brett |
| 6,413,278 B1 | 7/2002 | Marchosky |
| 6,416,551 B1 | 7/2002 | Keller |
| 6,419,706 B1 | 7/2002 | Graf |
| 6,447,448 B1 | 9/2002 | Ishikawa et al. |
| 6,454,806 B1 | 9/2002 | Cohen et al. |
| 6,468,310 B1 | 10/2002 | Ralph et al. |
| 6,475,639 B2 | 11/2002 | Shahinpoor et al. |
| 6,488,710 B2 | 12/2002 | Besselink |
| 6,517,580 B1 | 2/2003 | Ramadan et al. |
| 6,527,804 B1 | 3/2003 | Gauchet et al. |
| 6,533,818 B1 | 3/2003 | Weber et al. |
| 6,547,823 B2 | 4/2003 | Scarborough et al. |
| 6,565,605 B2 | 5/2003 | Goble et al. |
| 6,579,320 B1 | 6/2003 | Gauchet et al. |
| 6,582,466 B1 | 6/2003 | Gauchet |
| 6,582,468 B1 | 6/2003 | Gauchet |
| 6,592,624 B1 | 7/2003 | Fraser et al. |
| 6,595,998 B2 | 7/2003 | Johnson et al. |
| 6,607,558 B2 | 8/2003 | Kuras |
| 6,620,196 B1 | 9/2003 | Trieu |
| 6,626,943 B2 | 9/2003 | Eberlein et al. |
| 6,641,614 B1 | 11/2003 | Wagner et al. |
| 6,645,248 B2 | 11/2003 | Casutt |
| 6,648,917 B2 | 11/2003 | Gerbec et al. |
| 6,669,732 B2 | 12/2003 | Serhan et al. |
| 6,676,665 B2 | 1/2004 | Foley et al. |
| 6,682,562 B2 | 1/2004 | Viart et al. |
| 6,706,070 B1 | 3/2004 | Wagner et al. |
| 6,719,796 B2 | 4/2004 | Cohen et al. |
| 6,723,126 B1 | 4/2004 | Berry |
| 6,723,127 B2 | 4/2004 | Ralph et al. |
| 6,733,532 B1 | 5/2004 | Gauchet et al. |
| 6,733,535 B2 | 5/2004 | Michelson |
| 6,740,117 B2 | 5/2004 | Ralph et al. |
| 6,743,255 B2 | 6/2004 | Ferree |
| 6,758,861 B2 | 7/2004 | Ralph et al. |
| 6,770,094 B2 | 8/2004 | Fehling et al. |
| 6,770,095 B2 | 8/2004 | Grinberg et al. |
| 6,793,678 B2 | 9/2004 | Hawkins |
| 6,805,714 B2 | 10/2004 | Sutcliffe |
| 6,835,208 B2 | 12/2004 | Marchosky |
| 6,855,167 B2 | 2/2005 | Shimp et al. |
| 6,863,673 B2 | 3/2005 | Gerbec et al. |
| 6,881,229 B2 | 4/2005 | Khandkar et al. |

(56) References Cited

U.S. PATENT DOCUMENTS

| | | | |
|---|---|---|---|
| 6,893,464 B2 | 5/2005 | Kiester | |
| 6,936,071 B1 | 8/2005 | Marnay et al. | |
| 6,953,477 B2 | 10/2005 | Berry | |
| 6,955,691 B2 | 10/2005 | Chae et al. | |
| 6,964,686 B2 | 11/2005 | Gordon | |
| 6,966,910 B2 * | 11/2005 | Ritland | A61B 17/7004 606/257 |
| 6,969,404 B2 | 11/2005 | Ferree | |
| 7,018,412 B2 | 3/2006 | Ferreira et al. | |
| 7,018,416 B2 | 3/2006 | Hanson et al. | |
| 7,022,138 B2 | 4/2006 | Mashburn | |
| 7,025,787 B2 | 4/2006 | Bryan et al. | |
| 7,037,339 B2 | 5/2006 | Houfburg | |
| 7,083,650 B2 | 8/2006 | Moskowitz et al. | |
| 7,094,257 B2 | 8/2006 | Mujwid et al. | |
| 7,156,876 B2 | 1/2007 | Moumene et al. | |
| 7,211,112 B2 | 5/2007 | Baynham et al. | |
| 7,217,293 B2 | 5/2007 | Branch, Jr. | |
| 7,220,280 B2 | 5/2007 | Kast et al. | |
| 7,223,292 B2 | 5/2007 | Messerli et al. | |
| 7,226,483 B2 | 6/2007 | Gerber et al. | |
| 7,235,101 B2 | 6/2007 | Berry et al. | |
| 7,291,173 B2 | 11/2007 | Richelsoph et al. | |
| 7,320,708 B1 * | 1/2008 | Bernstein | A61F 2/44 623/17.15 |
| 7,326,248 B2 | 2/2008 | Michelson | |
| 7,442,211 B2 | 10/2008 | de Villiers et al. | |
| 7,503,920 B2 | 3/2009 | Siegal | |
| 7,503,933 B2 | 3/2009 | Michelson | |
| 7,507,241 B2 | 3/2009 | Levy et al. | |
| 7,517,363 B2 | 4/2009 | Rogers et al. | |
| 7,569,074 B2 | 8/2009 | Eisermann et al. | |
| 7,575,599 B2 | 8/2009 | Villiers et al. | |
| 7,618,458 B2 | 11/2009 | Biedermann et al. | |
| 7,621,950 B1 | 11/2009 | Globerman et al. | |
| 7,621,960 B2 | 11/2009 | Boyd et al. | |
| 7,641,692 B2 | 1/2010 | Bryan et al. | |
| 7,655,010 B2 | 2/2010 | Serhan et al. | |
| 7,691,147 B2 | 4/2010 | Gutlin et al. | |
| 7,703,727 B2 | 4/2010 | Selness | |
| 7,722,612 B2 | 5/2010 | Sala et al. | |
| 7,722,674 B1 | 5/2010 | Grotz | |
| 7,731,751 B2 | 6/2010 | Butler et al. | |
| 7,744,650 B2 | 6/2010 | Lindner et al. | |
| 7,749,270 B2 | 7/2010 | Peterman | |
| 7,771,473 B2 | 8/2010 | Thramann | |
| 7,789,914 B2 | 9/2010 | Michelson | |
| 7,799,080 B2 | 9/2010 | Doty | |
| 7,799,081 B2 | 9/2010 | McKinley | |
| 7,799,083 B2 | 9/2010 | Smith et al. | |
| 7,819,921 B2 | 10/2010 | Grotz | |
| 7,824,445 B2 | 11/2010 | Biro et al. | |
| 7,837,734 B2 | 11/2010 | Zucherman et al. | |
| 7,846,206 B2 | 12/2010 | Oglaza et al. | |
| 7,850,733 B2 | 12/2010 | Baynham et al. | |
| 7,854,766 B2 | 12/2010 | Moskowitz et al. | |
| 7,874,980 B2 | 1/2011 | Sonnenschein et al. | |
| 7,879,098 B1 | 2/2011 | Simmons, Jr. | |
| 7,887,589 B2 | 2/2011 | Glenn et al. | |
| 7,909,870 B2 | 3/2011 | Kraus | |
| 7,918,874 B2 | 4/2011 | Siegal | |
| 7,922,729 B2 | 4/2011 | Michelson | |
| 7,951,199 B2 | 5/2011 | Miller | |
| 7,959,675 B2 | 6/2011 | Gately | |
| 7,985,231 B2 | 7/2011 | Sankaran | |
| 7,993,403 B2 | 8/2011 | Foley et al. | |
| 8,016,859 B2 | 9/2011 | Donofrio et al. | |
| 8,021,424 B2 | 9/2011 | Beger et al. | |
| 8,021,426 B2 | 9/2011 | Segal et al. | |
| 8,025,697 B2 | 9/2011 | McClellan, III et al. | |
| 8,034,109 B2 | 10/2011 | Zwirkoski | |
| 8,043,381 B2 | 10/2011 | Hestad et al. | |
| 8,052,754 B2 | 11/2011 | Froehlich | |
| 8,057,545 B2 | 11/2011 | Hughes et al. | |
| 8,062,375 B2 | 11/2011 | Glerum et al. | |
| 8,075,621 B2 | 12/2011 | Michelson | |
| 8,097,036 B2 | 1/2012 | Cordaro et al. | |
| 8,105,382 B2 | 1/2012 | Olmos et al. | |
| 8,177,812 B2 | 5/2012 | Sankaran | |
| 8,192,495 B2 | 6/2012 | Simpson et al. | |
| 8,202,322 B2 | 6/2012 | Doty | |
| 8,216,312 B2 | 7/2012 | Gray | |
| 8,216,314 B2 | 7/2012 | Richelsoph | |
| 8,221,501 B2 | 7/2012 | Eisermann et al. | |
| 8,221,502 B2 | 7/2012 | Branch, Jr. | |
| 8,221,503 B2 | 7/2012 | Garcia et al. | |
| 8,231,681 B2 | 7/2012 | Castleman et al. | |
| 8,236,058 B2 | 8/2012 | Fabian et al. | |
| 8,241,358 B2 | 8/2012 | Butler et al. | |
| 8,241,361 B2 | 8/2012 | Link | |
| 8,257,442 B2 | 9/2012 | Edie et al. | |
| 8,262,666 B2 | 9/2012 | Baynham et al. | |
| 8,267,939 B2 | 9/2012 | Cipoletti et al. | |
| 8,267,965 B2 | 9/2012 | Gimbel et al. | |
| 8,273,128 B2 | 9/2012 | Oh et al. | |
| 8,287,599 B2 | 10/2012 | McGuckin, Jr. | |
| 8,292,959 B2 | 10/2012 | Webb et al. | |
| 8,303,663 B2 | 11/2012 | Jimenez et al. | |
| 8,323,345 B2 | 12/2012 | Sledge | |
| 8,328,852 B2 | 12/2012 | Zehavi et al. | |
| 8,337,559 B2 | 12/2012 | Hansell et al. | |
| 8,343,193 B2 | 1/2013 | Johnson et al. | |
| 8,353,961 B2 | 1/2013 | McClintock et al. | |
| 8,361,154 B2 | 1/2013 | Reo | |
| 8,366,777 B2 | 2/2013 | Matthis et al. | |
| 8,377,098 B2 | 2/2013 | Landry et al. | |
| 8,398,712 B2 | 3/2013 | de Villiers et al. | |
| 8,398,713 B2 | 3/2013 | Weiman | |
| 8,409,290 B2 | 4/2013 | Zamani et al. | |
| 8,409,291 B2 | 4/2013 | Blackwell et al. | |
| 8,414,650 B2 | 4/2013 | Bertele et al. | |
| 8,435,298 B2 | 5/2013 | Weiman | |
| 8,454,698 B2 | 6/2013 | de Villiers et al. | |
| 8,480,715 B2 | 7/2013 | Gray | |
| 8,480,742 B2 | 7/2013 | Pisharodi | |
| 8,486,148 B2 | 7/2013 | Butler et al. | |
| 8,491,659 B2 | 7/2013 | Weiman | |
| 8,506,635 B2 | 8/2013 | Palmatier et al. | |
| 8,518,087 B2 | 8/2013 | Lopez et al. | |
| 8,518,120 B2 | 8/2013 | Glerum et al. | |
| 8,545,567 B1 | 10/2013 | Krueger | |
| 8,551,173 B2 | 10/2013 | Lechmann et al. | |
| 8,556,979 B2 | 10/2013 | Glerum et al. | |
| 8,568,481 B2 | 10/2013 | Olmos et al. | |
| 8,579,977 B2 | 11/2013 | Fabian | |
| 8,579,981 B2 | 11/2013 | Lim et al. | |
| 8,591,585 B2 | 11/2013 | McLaughlin et al. | |
| 8,603,168 B2 | 12/2013 | Gordon et al. | |
| 8,603,177 B2 | 12/2013 | Gray | |
| 8,628,576 B2 | 1/2014 | Triplett et al. | |
| 8,628,578 B2 | 1/2014 | Miller et al. | |
| 8,632,595 B2 | 1/2014 | Weiman | |
| 8,636,802 B2 | 1/2014 | Serhan et al. | |
| 8,641,764 B2 | 2/2014 | Gately | |
| 8,663,329 B2 | 3/2014 | Ernst | |
| 8,668,740 B2 | 3/2014 | Rhoda et al. | |
| 8,679,183 B2 | 3/2014 | Glerum et al. | |
| 8,685,095 B2 | 4/2014 | Miller et al. | |
| 8,685,098 B2 | 4/2014 | Glerum et al. | |
| 8,696,751 B2 | 4/2014 | Ashley et al. | |
| 8,709,086 B2 | 4/2014 | Glerum | |
| 8,715,351 B1 | 5/2014 | Pinto | |
| 8,721,723 B2 | 5/2014 | Hansell et al. | |
| 8,728,166 B2 | 5/2014 | Schwab | |
| 8,753,398 B2 | 6/2014 | Gordon et al. | |
| 8,758,441 B2 | 6/2014 | Hovda et al. | |
| 8,764,806 B2 | 7/2014 | Abdou | |
| 8,771,360 B2 | 7/2014 | Jimenez et al. | |
| 8,778,025 B2 | 7/2014 | Ragab et al. | |
| 8,795,366 B2 | 8/2014 | Varela | |
| 8,795,374 B2 | 8/2014 | Chee | |
| 8,801,792 B2 | 8/2014 | de Villiers et al. | |
| 8,828,085 B1 | 9/2014 | Jensen | |
| 8,845,728 B1 | 9/2014 | Abdou | |

(56) References Cited

U.S. PATENT DOCUMENTS

| | | |
|---|---|---|
| 8,845,731 B2 | 9/2014 | Weiman |
| 8,845,732 B2 | 9/2014 | Weiman |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,900,307 B2 | 12/2014 | Hawkins et al. |
| 8,936,641 B2 | 1/2015 | Cain |
| 8,940,052 B2 | 1/2015 | Lechmann et al. |
| 9,089,428 B2 | 7/2015 | Bertele et al. |
| 9,095,446 B2 | 8/2015 | Landry et al. |
| 9,095,447 B2 | 8/2015 | Barreiro et al. |
| 9,387,087 B2 | 7/2016 | Tyber |
| 9,402,654 B2 | 8/2016 | Serhan |
| 9,414,923 B2 | 8/2016 | Studer et al. |
| 9,662,147 B2 | 5/2017 | Serhan et al. |
| 9,662,148 B2 | 5/2017 | Serhan et al. |
| 9,662,149 B2 | 5/2017 | Serhan et al. |
| 9,668,785 B2 | 6/2017 | Serhan et al. |
| 9,724,207 B2 | 8/2017 | DiMauro et al. |
| 2001/0018614 A1 | 8/2001 | Bianchi |
| 2001/0056302 A1 | 12/2001 | Boyer et al. |
| 2002/0010070 A1 | 1/2002 | Cales et al. |
| 2002/0032483 A1 | 3/2002 | Nicholson et al. |
| 2002/0035400 A1 | 3/2002 | Bryan et al. |
| 2002/0037799 A1 | 3/2002 | Li et al. |
| 2002/0039620 A1 | 4/2002 | Shahinpoor et al. |
| 2002/0068976 A1 | 6/2002 | Jackson |
| 2002/0068977 A1 | 6/2002 | Jackson |
| 2002/0128715 A1* | 9/2002 | Bryan .......... A61B 17/02 623/17.15 |
| 2002/0128716 A1 | 9/2002 | Cohen et al. |
| 2002/0151976 A1 | 10/2002 | Foley et al. |
| 2002/0165612 A1 | 11/2002 | Gerber et al. |
| 2003/0004575 A1 | 1/2003 | Erickson |
| 2003/0004576 A1 | 1/2003 | Thalgott |
| 2003/0006942 A1 | 1/2003 | Searls et al. |
| 2003/0014112 A1 | 1/2003 | Ralph et al. |
| 2003/0014116 A1 | 1/2003 | Ralph et al. |
| 2003/0023305 A1 | 1/2003 | McKay |
| 2003/0028251 A1 | 2/2003 | Mathews |
| 2003/0039620 A1 | 2/2003 | Rodriguez et al. |
| 2003/0040799 A1 | 2/2003 | Boyd et al. |
| 2003/0045939 A1 | 3/2003 | Casutt |
| 2003/0065396 A1 | 4/2003 | Michelson |
| 2003/0069642 A1 | 4/2003 | Ralph et al. |
| 2003/0078667 A1 | 4/2003 | Manasas et al. |
| 2003/0130739 A1 | 7/2003 | Gerbec et al. |
| 2003/0135275 A1 | 7/2003 | Garcia et al. |
| 2003/0135277 A1 | 7/2003 | Bryan et al. |
| 2003/0139812 A1 | 7/2003 | Garcia et al. |
| 2003/0139813 A1 | 7/2003 | Messerli et al. |
| 2003/0204261 A1 | 10/2003 | Eisermann et al. |
| 2003/0233145 A1 | 12/2003 | Landry et al. |
| 2004/0002761 A1 | 1/2004 | Rogers et al. |
| 2004/0010318 A1 | 1/2004 | Ferree |
| 2004/0030387 A1 | 2/2004 | Landry et al. |
| 2004/0049188 A1 | 3/2004 | Slivka et al. |
| 2004/0064144 A1 | 4/2004 | Johnson et al. |
| 2004/0073310 A1 | 4/2004 | Moumene et al. |
| 2004/0087947 A1 | 5/2004 | Lim et al. |
| 2004/0088055 A1 | 5/2004 | Hanson et al. |
| 2004/0127991 A1 | 7/2004 | Ferree |
| 2004/0133279 A1 | 7/2004 | Krueger et al. |
| 2004/0143332 A1 | 7/2004 | Krueger et al. |
| 2004/0153065 A1 | 8/2004 | Lim |
| 2004/0153156 A1 | 8/2004 | Cohen et al. |
| 2004/0162618 A1 | 8/2004 | Mujwid et al. |
| 2004/0172133 A1 | 9/2004 | Gerber et al. |
| 2004/0186570 A1 | 9/2004 | Rapp |
| 2004/0186577 A1 | 9/2004 | Ferree |
| 2004/0193273 A1 | 9/2004 | Huang |
| 2004/0193277 A1 | 9/2004 | Long et al. |
| 2004/0243238 A1 | 12/2004 | Amin et al. |
| 2004/0249462 A1 | 12/2004 | Huang |
| 2004/0267367 A1 | 12/2004 | O'Neil |
| 2005/0019365 A1 | 1/2005 | Frauchiger et al. |
| 2005/0038515 A1 | 2/2005 | Kunzler |
| 2005/0113916 A1 | 5/2005 | Branch |
| 2005/0113917 A1 | 5/2005 | Chae et al. |
| 2005/0119752 A1 | 6/2005 | Williams et al. |
| 2005/0125062 A1 | 6/2005 | Biedermann et al. |
| 2005/0165485 A1 | 7/2005 | Trieu |
| 2005/0197702 A1 | 9/2005 | Coppes et al. |
| 2005/0203624 A1 | 9/2005 | Serhan et al. |
| 2005/0222681 A1 | 10/2005 | Richley et al. |
| 2005/0256576 A1 | 11/2005 | Moskowitz et al. |
| 2005/0261769 A1 | 11/2005 | Moskowitz et al. |
| 2005/0278026 A1 | 12/2005 | Gordon et al. |
| 2006/0004431 A1 | 1/2006 | Fuller et al. |
| 2006/0058876 A1 | 3/2006 | McKinley |
| 2006/0058880 A1 | 3/2006 | Wysocki et al. |
| 2006/0100706 A1 | 5/2006 | Shadduck et al. |
| 2006/0111785 A1 | 5/2006 | O'Neil |
| 2006/0122701 A1 | 6/2006 | Kiester |
| 2006/0122703 A1 | 6/2006 | Aebi et al. |
| 2006/0136062 A1 | 6/2006 | DiNello et al. |
| 2006/0142858 A1 | 6/2006 | Colleran et al. |
| 2006/0206207 A1 | 9/2006 | Dryer et al. |
| 2006/0235531 A1 | 10/2006 | Buettner-Janz |
| 2006/0253201 A1 | 11/2006 | McLuen |
| 2006/0265075 A1 | 11/2006 | Baumgartner et al. |
| 2006/0265077 A1 | 11/2006 | Zwirkoski |
| 2006/0293753 A1 | 12/2006 | Thramann |
| 2007/0010886 A1 | 1/2007 | Banick et al. |
| 2007/0055377 A1 | 3/2007 | Hanson et al. |
| 2007/0118222 A1 | 5/2007 | Lang |
| 2007/0149978 A1 | 6/2007 | Shezifi et al. |
| 2007/0173939 A1 | 7/2007 | Kim et al. |
| 2007/0173940 A1 | 7/2007 | Hestad et al. |
| 2007/0178222 A1 | 8/2007 | Storey et al. |
| 2007/0191959 A1 | 8/2007 | Hartmann et al. |
| 2007/0198089 A1 | 8/2007 | Moskowitz et al. |
| 2007/0208423 A1 | 9/2007 | Messerli et al. |
| 2007/0219634 A1 | 9/2007 | Greenhalgh et al. |
| 2007/0233244 A1 | 10/2007 | Lopez et al. |
| 2007/0270968 A1 | 11/2007 | Baynham et al. |
| 2007/0272259 A1 | 11/2007 | Allard et al. |
| 2007/0276375 A1 | 11/2007 | Rapp |
| 2007/0299521 A1 | 12/2007 | Glenn et al. |
| 2008/0009877 A1 | 1/2008 | Sankaran et al. |
| 2008/0015701 A1 | 1/2008 | Garcia et al. |
| 2008/0021556 A1 | 1/2008 | Edie |
| 2008/0021558 A1 | 1/2008 | Thramann |
| 2008/0027550 A1 | 1/2008 | Link et al. |
| 2008/0033440 A1 | 2/2008 | Moskowitz et al. |
| 2008/0051902 A1 | 2/2008 | Dwyer |
| 2008/0058944 A1 | 3/2008 | Duplessis et al. |
| 2008/0065219 A1 | 3/2008 | Dye |
| 2008/0082173 A1 | 4/2008 | Delurio et al. |
| 2008/0132934 A1 | 6/2008 | Reiley et al. |
| 2008/0133017 A1 | 6/2008 | Beyar et al. |
| 2008/0140085 A1 | 6/2008 | Gately et al. |
| 2008/0140207 A1 | 6/2008 | Olmos et al. |
| 2008/0147193 A1 | 6/2008 | Matthis et al. |
| 2008/0161927 A1 | 7/2008 | Savage et al. |
| 2008/0167657 A1 | 7/2008 | Greenhalgh |
| 2008/0177388 A1 | 7/2008 | Patterson et al. |
| 2008/0183204 A1 | 7/2008 | Greenhalgh et al. |
| 2008/0195209 A1 | 8/2008 | Garcia et al. |
| 2008/0228225 A1* | 9/2008 | Trautwein .......... A61B 17/1606 606/246 |
| 2008/0243251 A1 | 10/2008 | Stad et al. |
| 2008/0243254 A1 | 10/2008 | Butler |
| 2008/0249622 A1 | 10/2008 | Gray |
| 2008/0281425 A1 | 11/2008 | Thalgott et al. |
| 2009/0005873 A1 | 1/2009 | Slivka et al. |
| 2009/0030423 A1 | 1/2009 | Puno |
| 2009/0054991 A1 | 2/2009 | Biyani et al. |
| 2009/0069895 A1 | 3/2009 | Gittings et al. |
| 2009/0076610 A1 | 3/2009 | Afzal |
| 2009/0099568 A1 | 4/2009 | Lowry et al. |
| 2009/0112320 A1 | 4/2009 | Kraus |
| 2009/0112324 A1 | 4/2009 | Refai et al. |

(56) References Cited

U.S. PATENT DOCUMENTS

| | | |
|---|---|---|
| 2009/0164020 A1 | 6/2009 | Janowski et al. |
| 2009/0177281 A1 | 7/2009 | Swanson et al. |
| 2009/0177284 A1 | 7/2009 | Rogers et al. |
| 2009/0222096 A1 | 9/2009 | Trieu |
| 2009/0222099 A1 | 9/2009 | Liu et al. |
| 2009/0234398 A1 | 9/2009 | Chirico et al. |
| 2009/0240335 A1 | 9/2009 | Arcenio et al. |
| 2009/0248159 A1 | 10/2009 | Aflatoon |
| 2009/0248163 A1 | 10/2009 | King et al. |
| 2009/0276051 A1 | 11/2009 | Arramon et al. |
| 2009/0292361 A1 | 11/2009 | Lopez |
| 2010/0016905 A1 | 1/2010 | Greenhalgh et al. |
| 2010/0042218 A1 | 2/2010 | Nebosky et al. |
| 2010/0076559 A1 | 3/2010 | Bagga et al. |
| 2010/0094426 A1 | 4/2010 | Grohowski, Jr. et al. |
| 2010/0179594 A1 | 7/2010 | Theofilos et al. |
| 2010/0211182 A1 | 8/2010 | Zimmermann |
| 2010/0234956 A1 | 9/2010 | Attia et al. |
| 2010/0262240 A1 | 10/2010 | Chavatte et al. |
| 2010/0286783 A1 | 11/2010 | Lechmann et al. |
| 2010/0324607 A1 | 12/2010 | Davis |
| 2011/0004308 A1 | 1/2011 | Marino et al. |
| 2011/0004310 A1 | 1/2011 | Michelson |
| 2011/0015747 A1 | 1/2011 | McManus et al. |
| 2011/0029082 A1 | 2/2011 | Hall |
| 2011/0035011 A1 | 2/2011 | Cain |
| 2011/0082552 A1 | 4/2011 | Wistrom et al. |
| 2011/0093074 A1 | 4/2011 | Glerum et al. |
| 2011/0093076 A1 | 4/2011 | Reo et al. |
| 2011/0130835 A1 | 6/2011 | Ashley et al. |
| 2011/0130838 A1 | 6/2011 | Morgenstern Lopez |
| 2011/0144753 A1 | 6/2011 | Marchek et al. |
| 2011/0159070 A1 | 6/2011 | Jin et al. |
| 2011/0172716 A1 | 7/2011 | Glerum |
| 2011/0270261 A1 | 11/2011 | Mast et al. |
| 2011/0282453 A1 | 11/2011 | Greenhalgh et al. |
| 2011/0301711 A1 | 12/2011 | Palmatier et al. |
| 2011/0301712 A1 | 12/2011 | Palmatier et al. |
| 2012/0004726 A1 | 1/2012 | Greenhalgh et al. |
| 2012/0004732 A1 | 1/2012 | Goel et al. |
| 2012/0022654 A1 | 1/2012 | Farris et al. |
| 2012/0029636 A1 | 2/2012 | Ragab et al. |
| 2012/0071977 A1 | 3/2012 | Oglaza et al. |
| 2012/0071980 A1 | 3/2012 | Purcell et al. |
| 2012/0083889 A1 | 4/2012 | Purcell et al. |
| 2012/0123546 A1 | 5/2012 | Medina |
| 2012/0136443 A1 | 5/2012 | Wenzel |
| 2012/0197403 A1 | 8/2012 | Merves |
| 2012/0226357 A1 | 9/2012 | Varela |
| 2012/0277869 A1 | 11/2012 | Siccardi et al. |
| 2012/0290097 A1 | 11/2012 | Cipoletti et al. |
| 2012/0310350 A1 | 12/2012 | Farris et al. |
| 2012/0310352 A1 | 12/2012 | DiMauro et al. |
| 2013/0030536 A1 | 1/2013 | Rhoda et al. |
| 2013/0030544 A1 | 1/2013 | Studer |
| 2013/0060337 A1 | 3/2013 | Petersheim et al. |
| 2013/0073044 A1 | 3/2013 | Gamache |
| 2013/0085572 A1 | 4/2013 | Glerum et al. |
| 2013/0085574 A1 | 4/2013 | Sledge |
| 2013/0110240 A1 | 5/2013 | Hansell et al. |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190876 A1 | 7/2013 | Drochner et al. |
| 2013/0190877 A1 | 7/2013 | Medina |
| 2013/0204371 A1 | 8/2013 | McLuen et al. |
| 2013/0211525 A1 | 8/2013 | McLuen et al. |
| 2013/0211526 A1 | 8/2013 | Alheidt et al. |
| 2013/0218276 A1 | 8/2013 | Fiechter et al. |
| 2013/0253585 A1 | 9/2013 | Garcia et al. |
| 2013/0261746 A1 | 10/2013 | Linares et al. |
| 2013/0310939 A1 | 11/2013 | Fabian et al. |
| 2014/0039622 A1 | 2/2014 | Glerum et al. |
| 2014/0046333 A1 | 2/2014 | Johnson et al. |
| 2014/0058513 A1 | 2/2014 | Gahman et al. |
| 2014/0067073 A1 | 3/2014 | Hauck |
| 2014/0086962 A1 | 3/2014 | Jin et al. |
| 2014/0107704 A1 | 4/2014 | Serhan et al. |
| 2014/0114414 A1 | 4/2014 | Abdou et al. |
| 2014/0114423 A1 | 4/2014 | Suedkamp et al. |
| 2014/0128977 A1 | 5/2014 | Glerum et al. |
| 2014/0128980 A1 | 5/2014 | Kirschman |
| 2014/0135934 A1 | 5/2014 | Hansell et al. |
| 2014/0142706 A1 | 5/2014 | Hansell et al. |
| 2014/0163683 A1 | 6/2014 | Seifert et al. |
| 2014/0172106 A1 | 6/2014 | To et al. |
| 2014/0180421 A1 | 6/2014 | Glerum et al. |
| 2014/0188225 A1 | 7/2014 | Dmuschewsky |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0257494 A1 | 9/2014 | Thorwarth et al. |
| 2014/0277476 A1 | 9/2014 | McLean et al. |
| 2014/0303731 A1 | 10/2014 | Glerum |
| 2014/0303732 A1 | 10/2014 | Rhoda et al. |
| 2014/0324171 A1 | 10/2014 | Glerum et al. |
| 2015/0088256 A1 | 3/2015 | Ballard |
| 2015/0238324 A1 | 8/2015 | Nebosky et al. |
| 2015/0374992 A1 | 12/2015 | Crosby et al. |
| 2016/0000476 A1 | 1/2016 | Serhan et al. |
| 2016/0038301 A1 | 2/2016 | Wickham |
| 2016/0058573 A1 | 3/2016 | DiMauro et al. |
| 2016/0067055 A1 | 3/2016 | Hawkins et al. |
| 2016/0074170 A1 | 3/2016 | Rogers et al. |
| 2016/0074175 A1 | 3/2016 | O'Neil |
| 2016/0100954 A1 | 4/2016 | Rumi et al. |
| 2016/0128843 A1 | 5/2016 | Tsau et al. |
| 2016/0249958 A1 | 9/2016 | Serhan et al. |
| 2016/0249959 A1 | 9/2016 | Serhan et al. |
| 2016/0249960 A1 | 9/2016 | Serhan et al. |
| 2016/0317714 A1 | 11/2016 | DiMauro et al. |
| 2016/0331415 A1 | 11/2016 | Serhan et al. |

FOREIGN PATENT DOCUMENTS

| | | |
|---|---|---|
| DE | 39 11 610 A1 | 10/1990 |
| DE | 40 12 622 C1 | 7/1991 |
| DE | 197 10 392 C1 | 7/1999 |
| DE | 20 2008 001 079 U1 | 3/2008 |
| EP | 0 282 161 A1 | 9/1988 |
| EP | 0 678 489 A1 | 10/1995 |
| EP | 1 290 985 A2 | 3/2003 |
| EP | 1 385 449 A2 | 2/2004 |
| EP | 1 532 949 A1 | 5/2005 |
| EP | 1 541 096 A1 | 6/2005 |
| EP | 1 285 449 B1 | 7/2006 |
| EP | 1 683 593 A2 | 7/2006 |
| EP | 1 698 305 B1 | 8/2007 |
| EP | 1 843 723 B1 | 3/2010 |
| EP | 2 368 529 A1 | 9/2011 |
| EP | 2 237 748 B1 | 9/2012 |
| EP | 2 641 571 A1 | 9/2013 |
| EP | 2 764 851 A1 | 8/2014 |
| FR | 2 718 635 A1 | 10/1995 |
| FR | 2 730 159 A1 | 8/1996 |
| FR | 2874814 | 3/2006 |
| JP | 2003-526457 A | 9/2003 |
| JP | 2006-516456 A | 7/2006 |
| JP | 2011-509766 A | 3/2011 |
| WO | 94/04100 A1 | 3/1994 |
| WO | 95/31158 A1 | 11/1995 |
| WO | 97/00054 A1 | 1/1997 |
| WO | 99/53871 A1 | 10/1999 |
| WO | 00/13620 A1 | 3/2000 |

(56) References Cited

FOREIGN PATENT DOCUMENTS

| WO | 00/53127 A1 | 9/2000 |
|---|---|---|
| WO | 00/74605 A1 | 12/2000 |
| WO | 01/01893 A1 | 1/2001 |
| WO | 01/01895 A1 | 1/2001 |
| WO | 01/17464 A1 | 3/2001 |
| WO | 2005/039455 A1 | 5/2005 |
| WO | 2005/112834 A2 | 12/2005 |
| WO | 2006/047587 A2 | 5/2006 |
| WO | 2006/058281 A2 | 6/2006 |
| WO | 2006/065419 A2 | 6/2006 |
| WO | 2006/081843 A1 | 8/2006 |
| WO | 2007/009107 A2 | 1/2007 |
| WO | 2007/028098 A2 | 3/2007 |
| WO | 2007/048012 A2 | 4/2007 |
| WO | 2007/084427 A2 | 7/2007 |
| WO | 2008/044057 A1 | 4/2008 |
| WO | 2009/064787 A2 | 5/2009 |
| WO | 2009/092102 A1 | 7/2009 |
| WO | 2009/124269 A1 | 10/2009 |
| WO | 2009/143496 A1 | 11/2009 |
| WO | 2010/068725 A2 | 6/2010 |
| WO | 2010/088766 A1 | 8/2010 |
| WO | 2010/148112 A1 | 12/2010 |
| WO | 2011/046459 A1 | 4/2011 |
| WO | 2011/046460 A1 | 4/2011 |
| WO | 2011/119617 A1 | 9/2011 |
| WO | 2011/142761 A1 | 11/2011 |
| WO | 2012/009152 A1 | 1/2012 |
| WO | 2012/028182 A1 | 3/2012 |
| WO | 2012/030331 A1 | 3/2012 |
| WO | 2012/089317 A1 | 7/2012 |
| WO | 2012/135764 A1 | 10/2012 |
| WO | 2013/006669 A2 | 1/2013 |
| WO | 2013/023096 A1 | 2/2013 |
| WO | 2013/025876 A1 | 2/2013 |
| WO | 2013/043850 A2 | 3/2013 |
| WO | 2013/082184 A1 | 6/2013 |
| WO | 2013/158294 A1 | 10/2013 |
| WO | 2013/173767 A1 | 11/2013 |
| WO | 2013/184946 A1 | 12/2013 |
| WO | 2014/014610 A1 | 1/2014 |
| WO | 2014/018098 A1 | 1/2014 |
| WO | 2014/026007 A1 | 2/2014 |
| WO | 2014/035962 A1 | 3/2014 |
| WO | 2014/088521 A2 | 6/2014 |
| WO | 2014/116891 A1 | 7/2014 |
| WO | 2015/048997 A1 | 4/2015 |

OTHER PUBLICATIONS

[No Author Listed] Porocoat® Porous Coating, Depuy Synthes Companies, 2015, 2 pages, webpage, accessed Jul. 5, 2016, <https://emea.depuysynthes.com/hcp/hip/products/qs/porocoat-porous-coating-emea>.

[No Author Listed] Spine Solutions—The non-fusion technology company, Brochure, Prodisc, Spine Solutions, Inc., 2001, 16 pages.

Cheng, B.C., Ph.D., Biomechanical pullout strength and histology of Plasmapore® XP coated implants: Ovine multi time point survival study. Aesculap Implant Systems, LLC, 2013, 12 pages.

Chiang, et al., Biomechanical Comparison of Instrumented Posterior Lumbar Interbody Fusion with One or Two Cages by Finite Element Analysis, Spine, 2006, pp. E682-E689, vol. 31 (19), Lippincott Williams & Wilkins, Inc.

European Search Report EP03253921.5, dated Nov. 13, 2003, 4 pages.

Folman, et al., Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).

Gore, Technique of Cervical Interbody Fusion, Clinical Orthopaedics and Related Research, 1984, pp. 191-195, No. 188.

Hoogland, T., et al., Total Lumbar Intervertebral Disc Replacement: Testing of a New Articulating Space in Human Cadaver Spines—24th Annual ORS, Dallas, TX, Feb. 21-23, 1978, 8 pages.

Hunt, et al., Expandable cage placement via a posterolateral approach in lumbar spine reconstructions, Journal of Neurosurgery: Spine, 2006, pp. 271-274, vol. 5.

International Patent Application No. PCT /US2013/029014, International Search Report dated Jul. 1, 2013, 2 pages.

Kotsias, A., Clinical trial of titanium-coated PEEL cages anterior cervical discectomy and fusion. [Klinishe Untersuching zum Einsatz von titanbeschichteten Polyetheretherketon-Implantaten bei der cervikalen interkorporalen fusion]. Doctoral thesis. Department of Medicine, Charite, University of Medicine Berlin, 2014, 73 pages. German language document.

Krbec, et al., [Replacement of the vertebral body with an expansion implant (Synex)], Acta Chir Orthop Traumatol Cech, 2002, pp. 158-162, vol. 69(3). Article in Czech. English Abstract Only.

Polikeit, et al., The importance of the end plate for interbody cages in the lumbar spine, Eur Spine J, 2003, pp. 556-561, vol. 12.

Shin, et al., Posterior Lumbar Interbody Fusion via a Unilateral Approach, Yonsei Medical Journal, 2006, pp. 319-325, vol. 47(3).

[No Author Listed] Porocoat® Porous Coating, Depuy Synthes Companies, 2017, 1 page, webpage, accessed Jul. 31, 2017, <https://emea.depuysynthes.com/hcp/hip/products/qs/porocoat-porous-coating-emea>.

U.S. Appl. No. 10/793,967, filed Mar. 6, 2004, Dynamized Interspinal Implant.

U.S. Appl. No. 14/134,090, filed Dec. 19, 2013, Dynamized Interspinal Implant.

U.S. Appl. No. 14/845,687, filed Sep. 4, 2015, Dynamized Interspinal Implant.

U.S. Appl. No. 15/148,937, filed May 6, 2016, Dynamized Interspinal Implant.

U.S. Appl. No. 15/149,085, filed May 7, 2016, Dynamized Interspinal Implant.

U.S. Appl. No. 15/149,132, filed May 8, 2016, Dynamized Interspinal Implant.

U.S. Appl. No. 15/219,505, filed Jul. 26, 2016, Dynamized Interspinal Implant.

U.S. Appl. No. 15/787,998, filed Oct. 19, 2017, Dynamized Interspinal Implant.

\* cited by examiner

DYNAMIZED INTERSPINAL IMPLANT

CROSS-REFERENCE TO RELATED APPLICATIONS

This application is a continuation of U.S. application Ser. No. 15/149,132, filed on May 8, 2016, which is a continuation of U.S. application Ser. No. 15/149,085, filed on May 7, 2016, which is a continuation of U.S. application Ser. No. 15/148,937, filed on May 6, 2016, which is a continuation of U.S. application Ser. No. 14/845,687, filed on Sep. 4, 2015 (now U.S. Pat. No. 9,402,654), which is a continuation of U.S. application Ser. No. 14/134,090, filed on Dec. 19, 2013 (now abandoned), which is a division of U.S. application Ser. No. 10/793,967, filed on Mar. 6, 2004 (now U.S. Pat. No. 8,636,802), each of which is hereby incorporated by reference in its entirety.

BACKGROUND OF THE INVENTION

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of articulation weight through a damaged, unstable vertebral joint.

In some cases, when a patient having a collapsed disc moves in extension (e.g., leans backward), the posterior portion of the annulus fibrosis or folding of the ligamentum flavum may further compress and extend into the spinal canal. This condition, called "spinal stenosis", narrows the spinal canal and causes impingement of tissue upon the spinal cord, thereby producing pain.

There have been numerous attempts to provide relief for these afflictions by providing a spacer that inserts between adjacent spinous processes present in the posterior portion of the spinal column. This spacer essentially lifts the upper spinous process off of the lower spinous process, thereby relieving stenosis. In general, these interspinous implants are adapted to allow flexion movement in the patient, but resist or limit extension.

U.S. Pat. No. 6,068,630 ("Zuchermann") discloses a spinal distraction implant that alleviates pain associated with spinal stenosis by expanding the volume in the spinal canal or neural foramen. Zuchermann discloses a plurality of implants having a body portion and lateral wings. The body portion is adapted to seat between the adjacent spinous processes, while the wings are adapted to prevent lateral movement of the body portion, thereby holding it in place between the adjacent spinous processes.

U.S. Pat. No. 5,645,599 ("Samani") attempts to relieve spinal stenosis by essentially inserting a flexible horseshoe-shaped device between the adjacent spinous processes. Although the Samani device desirably provides a self-limiting flexibility, it nonetheless suffers from some inadequacies. For example, the Samani device does not provide for natural physiologic rotational movement, nor for post-operative adjustment. In addition, the Samani device discloses the insertion of a bearing cushion, and the adhesive bonding of the bearing cushion to the horseshoe element. However, it is believed that mere adhesive bonding of these elements would cause the cushion to be prone to migration.

SUMMARY OF THE INVENTION

The present inventors have developed a number of flexible interspinous devices having a number of desirable features providing improved performance over conventional solutions.

In a first embodiment, the device has a flexible anterior wall having a narrowed portion. The narrowed portion allows the device to twist in response to spinal rotation, thereby more closely mimicking natural physiologic movement.

Therefore, in accordance with the first embodiment of the present invention, there is provided an interspinous implant for insertion between adjacent spinous processes, the implant comprising:
   a) a flexible body comprising:
      i) an upper posterior portion having an upper surface adapted to bear upon an upper spinous process,
      ii) a lower posterior portion having a lower surface adapted to bear upon a lower spinous process, and
      iii) an arcuate, flexible anterior wall connecting the upper and lower portions,
   wherein the anterior wall has a narrowed portion.

In a second embodiment, the device has a cushion portion interdigitated with each of the upper and lower bearing portions. Because the cushion portion is interdigitated with these elements, a tenacious bond is provided and migration concerns are alleviated.

Therefore, in accordance with the second embodiment of the present invention, there is provided an interspinous implant for insertion between adjacent spinous processes, the implant comprising:
   a) a flexible body comprising:
      i) an upper posterior portion having an upper surface adapted to bear upon an upper spinous process,
      ii) a lower posterior portion having a lower surface adapted to bear upon a lower spinous process,
      iii) an arcuate, flexible anterior wall connecting the upper and lower portions, and
   b) a cushion element having an upper surface and a lower surface,
wherein the lower surface of the upper portion of the flexible body comprises a porous coating thereon, and wherein the upper surface of the cushion element is interdigitated with the porous coating.

In a third embodiment, the device is adapted to be post-operatively adjustable. The adjustability allows the device to respond to an altered physiologic state, such as an increased collapse of the disc space or decreased patient flexibility, by adjusting the overall stiffness of the implant.

Therefore, in accordance with the third embodiment of the present invention, there is provided an interspinous implant for insertion between adjacent spinous processes, the implant comprising:
   a) a flexible body comprising:
      i) an upper posterior portion having an upper surface adapted to bear upon an upper spinous process,
      ii) a lower posterior portion having a lower surface adapted to bear upon a lower spinous process,
      iii) an arcuate, flexible anterior wall connecting the upper and lower posterior portions, and
      iv) means for adjusting the stiffness of the implant.

DETAILED DESCRIPTION OF THE FIGURES

Figure 6:
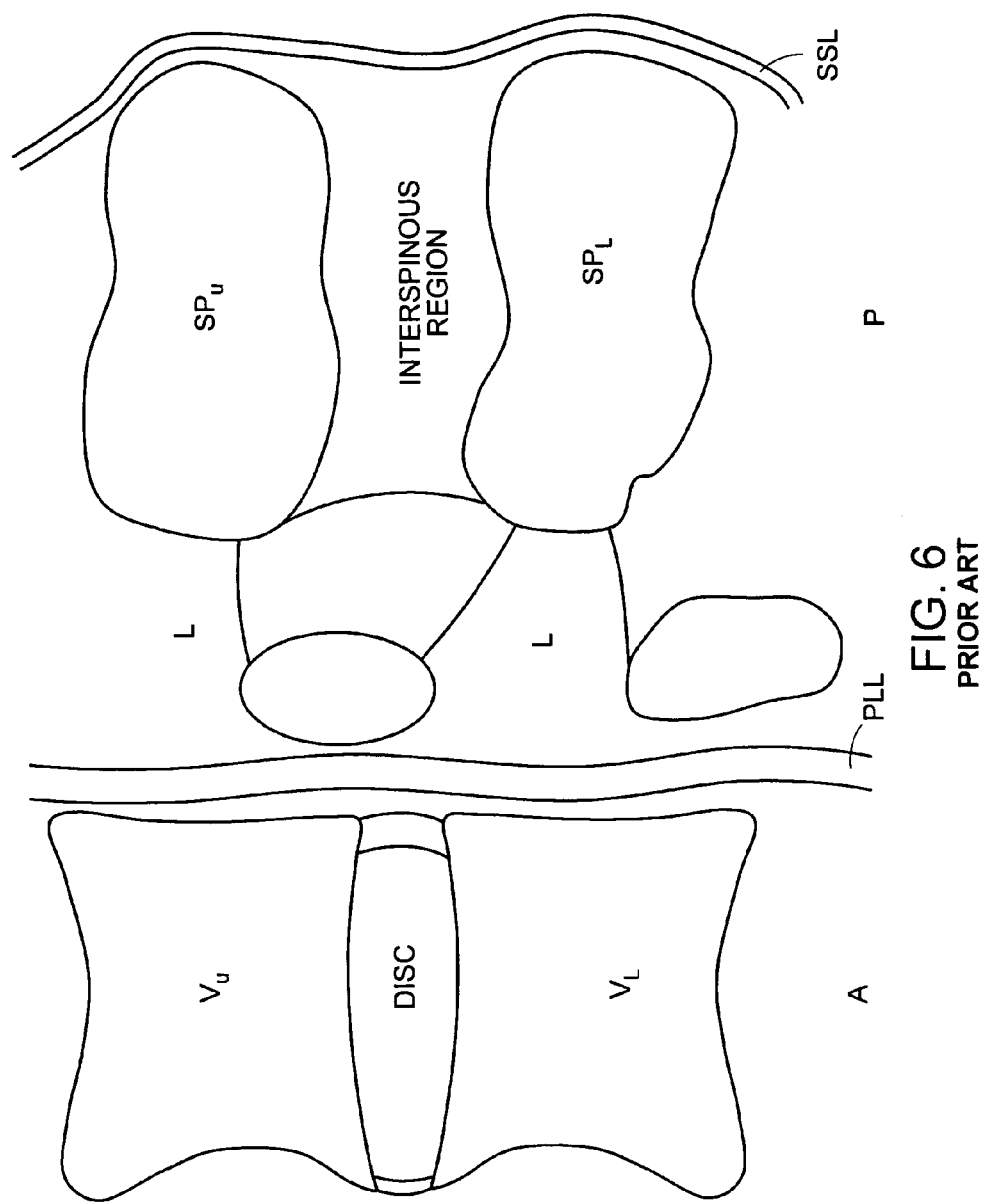
FIG. 6 is a side view of a functional spinal unit of the human anatomy.

For the purposes of the present invention, the term "interspinous" refers to the volume located between two adjacent spinous processes of adjacent vertebrae. The terms "anterior" and "posterior" are used as they are normally used in spinal anatomy. Accordingly, the "anterior" portion of the interspinous device is that portion rests relatively close to the spinal cord, while the "posterior" portion of the interspinous device is that portion rests relatively close to the skin on the patient's back. Now referring to FIG. 6, there is provided an anatomic "functional spinal unit" or FSU comprising an upper vertebrae Vu having an upper vertebral body $VB_U$ and an upper spinous process SPu, a lower vertebra having a lower vertebral body $VB_L$ having a lower spinous process $SP_L$. The vertebral bodies lies in the anterior A portion of the FSU, while the spinous processes lie in the posterior portion P of the FSU. Disposed between the vertebral bodies is a disc space DISC. Disposed between the spinous process is an "interspinous region" . . . . Disposed between the spinous process and the vertebral body of each vertebra is a lamina L. The supraspinous ligament SSL lies posterior to the spinous processes. The Posterior longitudinal ligament PLL lies posterior to the vertebral bodies.

Figures 1A, 1B:
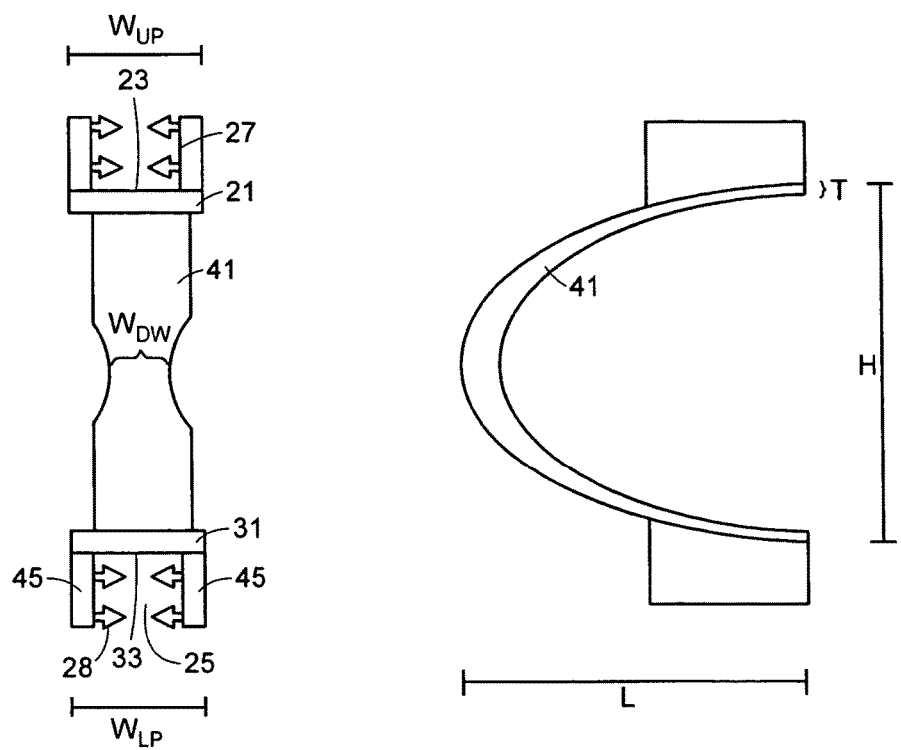
FIG. 1a is a posterior view of the first embodiment of the interspinous implant in the coronal plane
FIG. 1b is a side view of the first embodiment of the interspinous implant in the saggital plane.

Now referring to FIGS. 1a and 1b, there is provided an interspinous implant 1 for insertion between adjacent spinous processes, the implant comprising:
  a) a flexible body 11:
    i) an upper posterior portion 21 having an upper surface 23 adapted to bear upon an upper spinous process and a width $W_{UP}$,
    ii) a lower posterior portion 31 having a lower surface 33 adapted to bear upon a lower spinous process and a width $WL_P$, and
    iii) a flexible arcuate anterior wall 41 connecting the upper and lower portions and having a narrowed portion 43 defining a minimum width $W_{DW}$,
wherein the minimum width of the anterior wall is less than the width $W_{UP}$ of the upper portion.

Figure 1C:
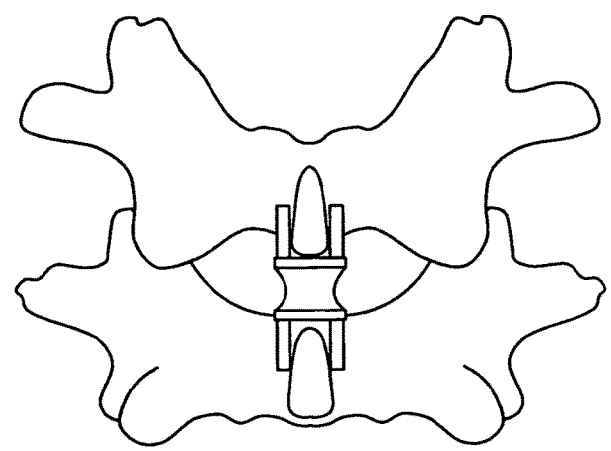
FIG. 1c is a posterior view of the first embodiment of the interspinous implant implanted between adjacent vertebrae.

Now referring to FIG. 1c, in use, the implant of FIGS. 1a and 1b is inserted into the interspinous region of an functional spinal unit (FSU), that is, between the adjacent spinous processes. The U-shaped body has a stiffness and geometry adapted to provide the desired spacing between the upper and lower process. In addition, in preferred embodiments, the U-shaped body is adapted to be somewhat flexible, so that it somewhat restricts the extent of extension motion of the FSU.

In preferred embodiments, the flexible body is U-shaped. In other embodiments, the flexible body has a posterior wall (preferably, arcuate) that flexibly connects the posterior portions of the upper and lower bearing surfaces of the flexible body to provide an overall substantially oval shape.

Preferably, the flexible body has a configuration and is made of a material that provides a first stiffness that limits the range of motion of the FSU. In some embodiments, the flexible body stiffness provides at least 50% of the overall initial stiffness of the implant, preferably at least 75%, more preferably at least 90%.

Preferably, the flexible body is adapted to provide a stiffness of between 50 N/mm and 1000 N/mm, more preferably between 100 N/mm and 500 N/mm. When the flexible body stiffness is in this range, it maintains the flexion/extension ROM of a normal lumbar FSU to less than 20 degrees, with less than 13 degrees of motion in flexion and less than 7 degrees of motion in extension. Preferably, the typical displacement of the posterior ends of the device under physiologic loading in the saggital plane is in the range of 1-6 mm.

The flexible can be made of a suitable biocompatible material typically used in structural spinal applications, including metals, plastics and ceramics. In some embodiments, the flexible body is made of a material selected from the group consisting of titanium alloy (including memory metals and superelastic alloys), stainless steel, and chrome cobalt. Preferably, the flexible body is provided in a sterile form.

Now referring to FIG. 1, in some embodiments, the flexible body has a height H of between 10 mm and 20 mm; a thickness T of between 1 mm and 2 mm; a length L of between 20 mm and 30 mm, and a width W of between 3 and 20 mm, preferably between 5 mm and 10 mm. In these embodiments, the implant can be easily inserted between typical adjacent spinous processes.

In some embodiments, the flexible body has a longitudinal cross section having a horseshoe shape. In others, the longitudinal cross-section describes a circle. In others, it is a pill shape. In others, it is substantially oval. In some embodiments, the upper and lower posterior portions are substantially non-parallel.

In some embodiments, as shown in FIG. 1b, the upper and lower posterior portions of the flexible body each have a longitudinal recess 25 defining a bearing surface 23, 33 and opposing recess walls 27. The recess shape is adapted to receive projecting portions of the opposed spinous processes, thereby securing the U-shaped shell between the spinous processes. In some embodiments, the recess walls have teeth 28 extending inwardly therefrom that provide a more grip upon the spinous processes. In some embodiments, at least the bearing surfaces of the recess have teeth 415 (as shown in FIG. 4c) extending outwardly therefrom that provide a more grip upon the spinous processes.

In some embodiments, the recess 25 defines an upper pair of extensions 45 extending from the bearing surface 33 and collectively defining a bracket. Each extension may comprise a transverse throughhole (not shown) adapted for fixing the implant to the adjacent spinous processes.

In some embodiments, each extension comprises a transverse throughhole adapted for fixing the implant to the adjacent spinous processes. In some embodiments, the implant further comprises a fastening element having a first end extending through the first transverse throughole and a second end extending through the second transverse through-hole.

The flexible body of the present invention preferably has a flexible anterior wall connecting the upper and lower portions of the U-shaped body, thereby providing a spring quality to the U-shaped body for flexibly resisting extreme FSU extension. This flexible anterior wall is preferably shaped to conform with the opposed surfaces of the opposing spinous processes (as shown in FIG. 1c). This quality also insures the grip of the implant and reduces unwanted stresses upon the flexible body. In some embodiments, the thickness of the distal wall is greater than the thickness of the posterior portions.

Figure 2A:
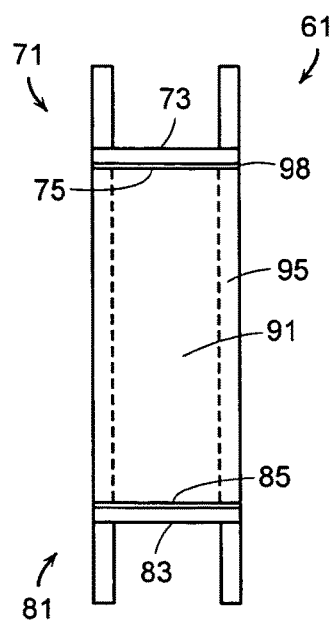
FIG. 2a is a posterior view of the second embodiment of the interspinous implant.
Figure 2B:
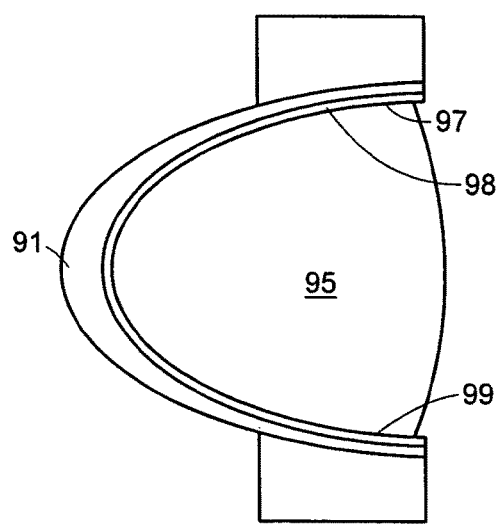
FIG. 2b is a side view of the second embodiment of the interspinous implant in the saggital plane.

Now referring to FIGS. 2a and 2b, there is provided an interspinous implant 51 for insertion between adjacent spinous processes, the implant comprising:
- a) a flexible U-shaped body 61:
    - i) an upper portion 71 having an upper surface 73 adapted to bear upon an upper spinous process and a lower surface 75,
    - ii) a lower portion 81 having a lower surface 83 adapted to bear upon a lower spinous process and an upper surface 85,
    - iii) a flexible distal wall 91 connecting the upper and lower portions, and
- b) a cushion element 95 having an upper surface 97 and a lower surface 99, wherein the lower surface of the upper portion of the flexible body comprises a porous coating 98 thereon, and wherein the upper surface of the cushion element is interdigitated with the porous coating.

In use, the cushion element provides a dampening effect upon natural extension. The interdigitated nature of the cushion bond reduces migration concerns.

In some embodiments, the bonding covers substantially the entire extent of the inner surface of the U-shaped body (i.e., the upper surface of the cushion is bonded to the lower surface of the upper posterior portion, the anterior surface of the cushion is bonded to the posterior surface of the flexible anterior wall, and the lower surface of the cushion is bonded to the upper surface of the lower posterior portion).

Figure 2C:
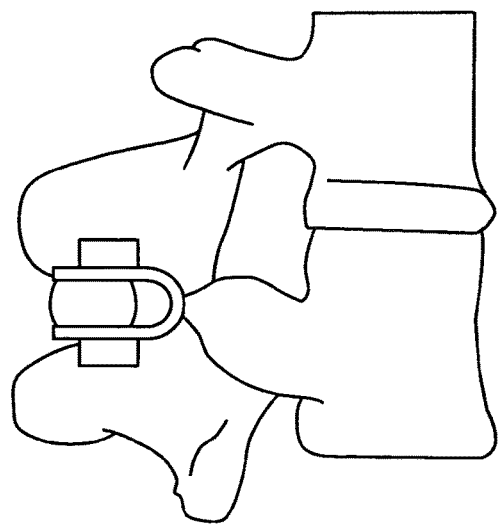
FIG. 2c is a side view of an embodiment of the interspinous implant implanted between adjacent vertebrae.

Now referring to FIG. 2c, in some embodiments, the bonding covers only the posterior portions of the inner surface of the U-shaped body (i.e., the lower surface of the upper posterior portion, and the upper surface of the lower posterior portion, but not the posterior surface of the flexible anterior wall). The partial coverage of this embodiment provides an amount of stress relief to the cushion-U-shaped body interface.

The cushion element of FIGS. 2a-2b is preferably made of an elastomeric material, more preferably a polyolefin rubber or carbon black reinforced polyolefin rubber. The hardness of the elastomeric cushion element is preferably between 56 and 72 shore A durometer. The ultimate tensile strength of the cushion element is preferably greater than 1600 psi. The cushion element preferably has an ultimate elongation greater than 300% using the ASTM D412-87 testing method, and a tear resistance greater than 100 psi using the ASTM D624-86 testing method. Although the cushion element is preferably a polyolefin rubber, it can be made of any elastomeric material that simulates the response of the natural ligaments.

Still referring to FIG. 2a, a porous coating 98 is provided as the inner surface of the U-shaped body. The porous coating provides an opportunity for the cushion element to interdigitate with the porous coating, and so obtain a greater amount of surface contact between the U-shaped body and the cushion, thereby achieving a lower maximum stress. In some embodiments, the coating covers the entire extent of the inner surface of the U-shaped body (i.e., the upper surface of the cushion is bonded to the lower surface of the upper posterior portion, the anterior surface of the cushion is bonded to the posterior surface of the flexible anterior wall, and the lower surface of the cushion is bonded to the upper surface of the lower posterior portion). Preferably, the coating comprises a layer of small spherical particles or beads.

In some embodiments, the coating covers only the posterior portions of the inner surface of the U-shaped body (i.e., the lower surface of the upper posterior portion, and the upper surface of the lower posterior portion, but not the posterior surface of the flexible anterior wall).

In some embodiments, a coating may also be applied to the superior side of the upper portion and the inferior side of the lower portion to promote bony ingrowth and osteointegration. In some embodiments thereof, and the coating may include beads, and may have osteobiologic components such as hydroxyapatite or tricalcium phosphate.

The present inventors have noted that there may be a need to correct the range of motion (ROM) provided by a motion disc after the motion disc has been implanted and there is need to change the load transferred through the facet joints to alleviate pain and facet joint degeneration.

For example, because implantation of spinal prostheses is an inexact procedure, there may be times when implantation provides too much or too little motion. For example, in some implantation procedures, damage to the anterior longitudinal ligament (ALL) is contemplated. Because the ALL in its physiologic form restricts the flexion/extension range of the natural disc, damage to it may provide the implanted disc with an unacceptably large range of motion (ROM) in flexion and extension. This overly large ROM is problematic because it produces atypical loads upon the facet joints as well as the adjacent intervertebral discs, thereby leading to premature degeneration of those facet joints and intervertebral discs. Accordingly, there may be a need to post-operatively correct the ROM of the implant in order to fine tune the ROM.

In another example, an implanted disc has an acceptable ROM at the time of implantation, but the patient undergoes typical aging so that the patient's normal range of motion decreases over time. In this case, it may be desirable to decrease the implant ROM so that it corresponds with the patient's natural decreased ROM.

Accordingly, there may be a need to post-operatively correct the ROM of the implant in order to adjust the implant ROM to the new needs of the patient.

The implant of the present invention is advantageous because it can be inserted into the spine at a first stiffness, and then adjusted to a second stiffness to meet the needs of the particular patient.

In a first preferred embodiment, the stiffness of the implant is adjusted post-operatively in order to fine tune the implant to the surgical needs of the patient.

In a second preferred embodiment, the stiffness of the implant is adjusted in order to fine tune the implant to the changing post-surgical needs of the patient.

In many embodiments, the stiffness of the implant is increased in order to reduce the ROM of a functional spinal unit (FSU).

Figure 3A:
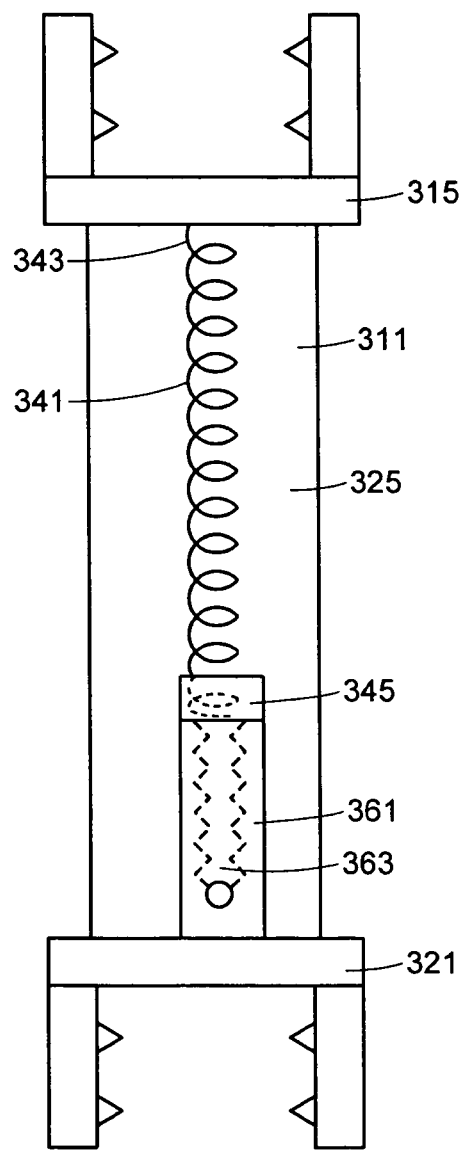
FIG. 3a is a posterior view of the third embodiment of the interspinous implant.
Figure 3B:
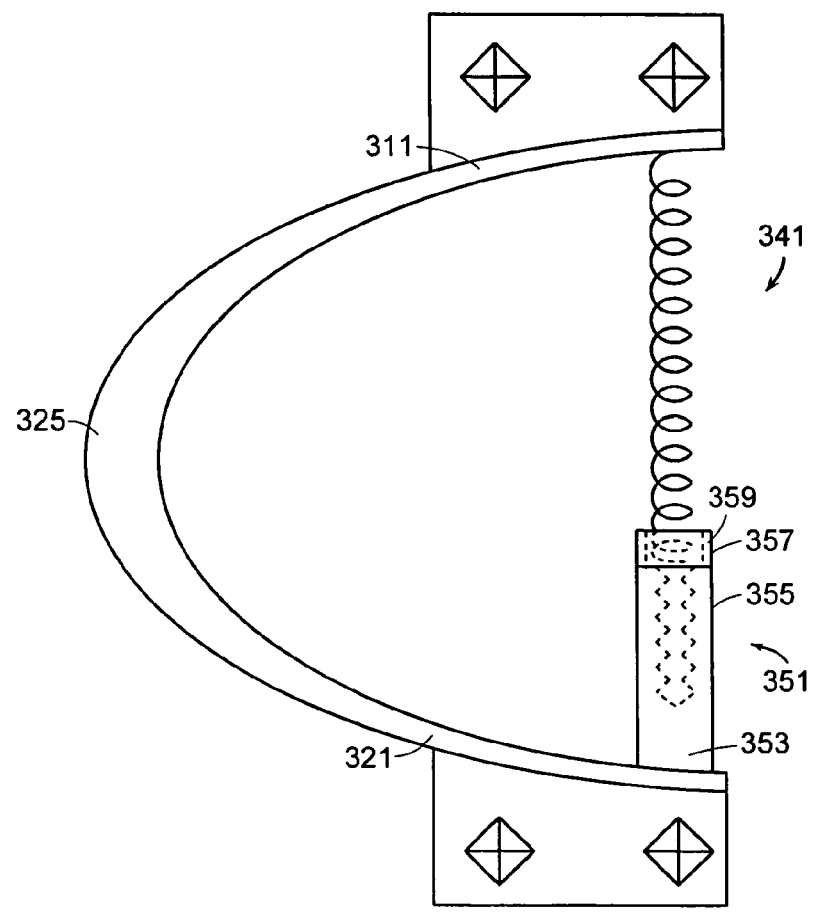
FIG. 3b is a side view of the third embodiment of the interspinous implant in the saggital plane.

In some embodiments, the implant further comprises a compression spring, and the overall stiffness of the implant is changed by adjusting the length of the compression spring. Now referring to FIGS. 3a-3b, in some embodiments, there is provided an interspinous implant 301 for insertion between adjacent spinous processes, the implant comprising:

a) a flexible outer shell 311 comprising:
        i) an upper posterior portion 315 adapted to bear upon an upper spinous process,
        ii) a lower posterior portion 321 adapted to bear upon a lower spinous process,
        iii) a flexible anterior wall 325 connecting the upper and lower posterior portions,
    b) a compression spring 341 having an upper portion 343 and a lower portion 345, the upper portion of the compression screw being attached to the upper posterior portion of the flexible outer shell, and
    c) a worm screw 351 having a lower portion 353 connected to the lower posterior portion and an upper portion 355 contacting the lower portion of the compression spring.

In this particular embodiment, the upper portion of the worm screw comprises a cup 357 having an annular sidewall 359 extending upward. The lower end portion of the compression spring is not rigidly attached to the cup, but rather sits freely in the annulus and bears against the cup. Containment by the cup allows the upper end of the worm screw to simply bear against the lower end of the spring without requiring rigid connection thereto.

In use, actuation of the worm screw causes inner thread 363 of the worm screw to turn relative to the outer cylinder 361 of the worm screw. The outer cylinder 361 responds by moving axially upward, thereby forcing compression of the compression spring, and increasing the effective resistance of the device to axial compression.

Figure 4A:
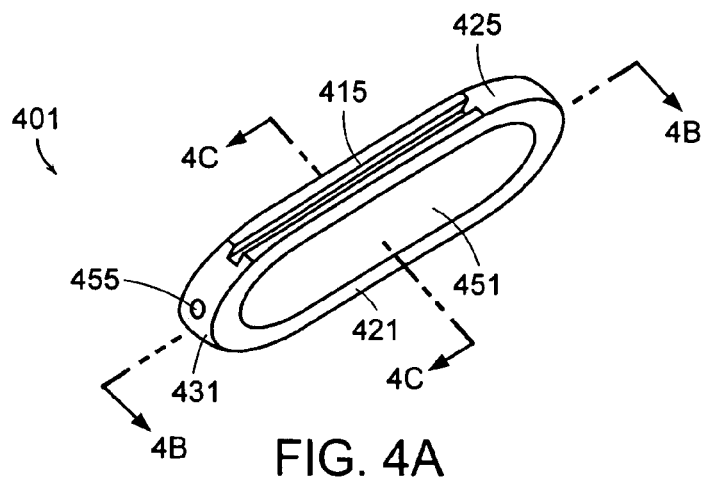
FIGS. 4a-4c are perspective, longitudinal and frontal cross-sectional views of a fourth embodiment of the present invention.
Figure 4B:
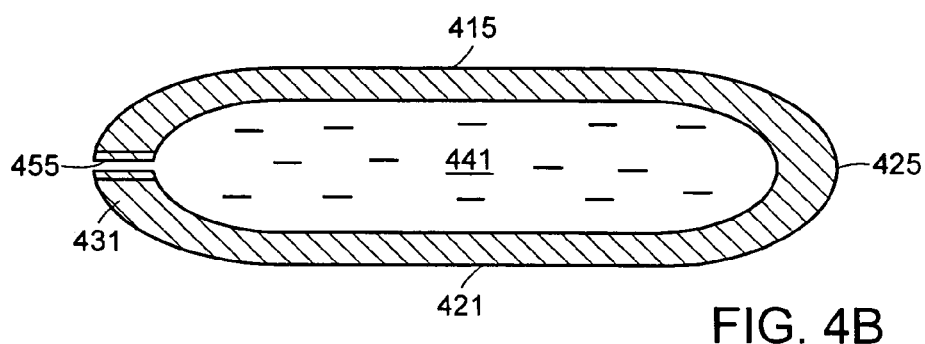
Figure 4C:
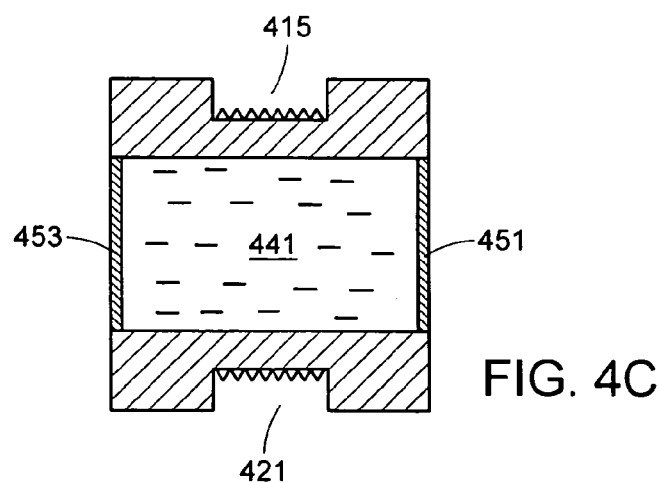
Figure 4D:
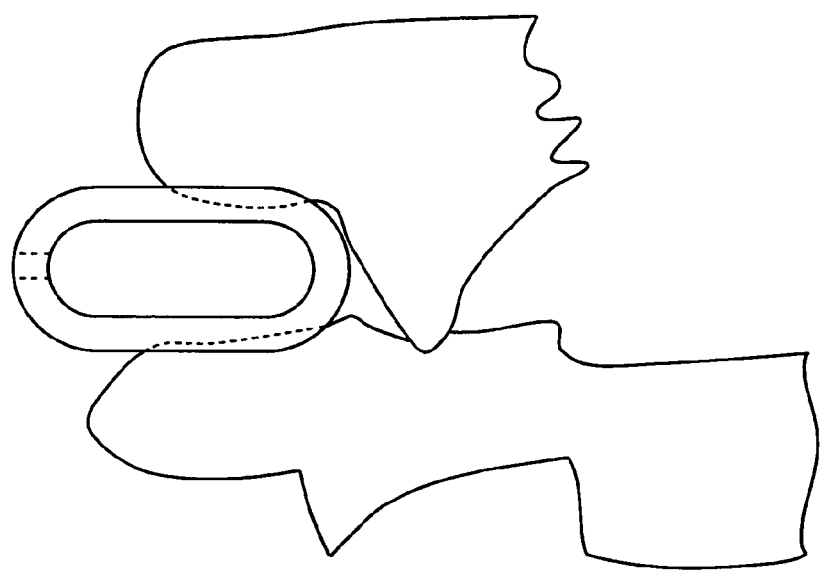
FIG. 4d is a side view of the fourth embodiment of the interspinous implant implanted between adjacent vertebrae.

Now referring to FIGS. 4a-4c, in some embodiments, there is provided an interspinous implant 401 for insertion between adjacent spinous processes, the implant having an implant stiffness and comprising:

a) a flexible outer shell 411 having a shell stiffness and comprising:
        i) an upper surface 415 adapted to bear upon an upper spinous process,
        ii) a lower surface 421 adapted to bear upon a lower spinous process,
        iii) an arcuate anterior wall 425 connecting the upper and lower surfaces, and
        iv) an arcuate posterior wall 431 extending between the upper and lower surfaces,
    b) compliant side walls 451,453, extending between the upper and lower surfaces, and
    c) an inner core 441 (such as a hydrogel) contained within the shell, wherein the inner core has an adjustable stiffness.

When it is desired to decrease the range of motion ("ROM") of the functional spinal unit ("FSU"), the stiffness of the core material may be increased, thereby increasing the stiffness of the implant and its resistance to an axial load. The resulting increase in the stiffness of the interspinous implant provides a more substantial resistance to extension, thereby desirably decreasing the ROM of the FSU to correspond with the needs of the patient.

Similarly, when it is desired to increase the range of motion ("ROM") of the functional spinal unit ("FSU"), the stiffness of the core material is decreased, thereby decreasing the stiffness of the implant and its resistance to an axial load. The resulting decrease in the stiffness of the interspinous implant reduces resistance to extension, thereby desirably increasing the ROM of the FSU to correspond with the needs of the patient.

The implant of this embodiment of the present invention also has a flexible posterior wall extending between the upper and lower portions of the U-shaped body. This posterior wall is preferably arcuate and preferably connects the upper surface of the lower portion and the lower surface of the upper portion of the U-shaped body to form a substantially oval body (as shown). In this condition, the posterior wall provides substantial closure to the U-shaped body. Accordingly, adjustment of the stiffness of the core material residing within the outer shell increases or decreases the stiffness of the implant.

The compliance of the sidewalls is selected to correspond with the level of resistance desired by the implant. For example, in some embodiments (as in FIG. 4a-4c,) the sidewalls are very thin and may be made of a very flexible material, such as a plastic weave. In these embodiments, the high compliance of the sidewalls will allow the core material to bulge laterally in response to an axial load, thereby tempering the resistance provided by the core material to the axial load.

In other embodiments, however, the sidewalls can be made of metal, and even be integral with the outer shell. In these embodiments, the sidewalls will be flexible but more rigid than a plastic membrane. In these embodiments, the relative rigidity of the sidewalls will not allow the core material to bulge significantly laterally, thereby augmenting the resistance provided by the core material to the axial load.

Preferably, the core is a fluid material contained within the cavity of the shell and is made of a material having a quality whose adjustment will produce a change in the stiffness of the implant. When the stiffness of the core is adjusted, the overall stiffness of the implant correspondingly changes. In some embodiments, the core has a first stiffness and contributes between 10 and 20% of the overall initial stiffness of the implant. In such embodiments, the stiffness of the core is increased to a second stiffness that increases the overall initial stiffness of the implant up to at least 40% to provide an adjusted implant stiffness of at least 300 N/mm, and more preferably at least 500 N/mm. When the implant stiffness is in this range, the implant can by itself provide sufficient stiffness to reduce the extension of a normal lumbar FSU to less than 7 degrees, preferably less than 5 degrees.

Preferably, the core material is selected to be sensitive to an external stimulus, which, when applied, stimulates the core material to adjust its stiffness from a first stiffness to a second stiffness. In some embodiments, the stimulus stimulates the core to increase its stiffness. In some embodiments, the stimulus stimulates the core to lower its stiffness.

Preferably, the core material is sensitive to a stimulus selected from the group consisting pH, light, and electric current.

In preferred embodiments, the core material comprises a hydrogel. In preferred embodiments, the hydrogel undergoes expansion when stimulated by a decreased pH. The resulting expansion of the core material increases the stiffness of the core, thereby increasing the stiffness of the implant and providing increased resistance to extension by the FSU. In some embodiments, the hydrogel is selected from ionic polymers disclosed in US Published Patent Application No. 2002/0039620, the specification of which is incorporated by reference in its entirety. In some embodiments, the hydrogel is selected from ionic polymers disclosed in U.S. Pat. No. 6,475,639, the specification of which is incorporated by reference in its entirety.

When pH is selected as the stimuli, in some embodiments, an acid or a base is introduced into the core material from an ex vivo source. For example, the acid or base can be administered subcutaneously via a hypodermic needle and introduced into the core material through a fluid port 455.

The provision of a fluid port provides the surgeon with the flexibility to selected the amount of acid or base needed to suit the needs of the patient.

In other embodiments in which pH is selected as the stimuli, the implant further comprises a container that individually houses and sequesters the acid or base from the core material. For example, the acid or base can be sequestered in a valved, separate compartment within the shell that is in fluid connection with the cavity housing the core material. The valve is opened (for example, by telemetry), the acid or base enters the cavity housing the core material and mixes with the core material. The resulting pH change causes a change in the specific volume of the core material, thereby increasing or decreasing the stiffness of the core material and the overall implant. The advantage of this embodiment is that the stiffness of the implant is changed through a completely non-invasive technique.

In some embodiments (not shown), the device could be made of a shape memory metal having a relatively flexible property during the martensitic phase and a relatively stiff property in the austenitic phase. In one embodiment, this memory metal device could be implanted in its flexible martensitic phase. If the clinician desires to increase the stiffness of the implant, the clinician could raise the temperature of the device (by heating) to a temperature above its austenitic phase, thereby increasing the stiffness of the device and increasing its resistance to an axial compressive load.

In some embodiments of the present invention, the implant further comprises smart features for helping the surgeon monitor and react to the changing conditions of the implanted device.

In some embodiments, a sensing means is also used with the implant of the present invention. This sensing means analyzes physical surroundings. Its purpose is to identify when a significant change has occurred which could warrant adjusting the stiffness of the implant. The sensor can be contained within the implant, or provided as a stand alone entity.

In some embodiments, a reporting means for reporting the findings of the sensors to an ex vivo source is also used with the implant of the present invention. The reporter can be contained within the implant, or provided as a stand alone entity.

In some embodiments, a receiver for receiving ex vivo-generated information is also used with the implant of the present invention. The receiver can be contained within the implant, or provided as a stand alone entity.

In some embodiments, the implant comprises two shells having flexible anterior walls extending in the same direction, wherein the stiffness is adjusted by adjusting the distance between the respective flexible anterior walls. Now referring to FIG. 5a, there is provided an interspinous implant 501 for insertion between adjacent spinous processes, the implant comprising:
   a) a flexible outer shell 511 comprising:
   i) an upper posterior portion 515 adapted to bear upon an upper spinous process and having a lower end 517 having a first set of teeth 519,
   ii) a lower posterior portion 521 adapted to bear upon a lower spinous process and having a upper end 522 having a second set of teeth 523,
   iii) a flexible anterior wall 525 connecting the upper and lower posterior portions of the flexible outer shell,
   b) a flexible inner shell 551 comprising:
   i) an upper posterior portion 555 having an upper end 556 having a third set of teeth 557 engaged in the first set of teeth,
   ii) a lower posterior portion 571 having a lower end 573 having fourth set of teeth 577 engaged in the second set of teeth,
   iii) a flexible anterior wall 575 connecting the upper and lower posterior portions.

Figure 5A:
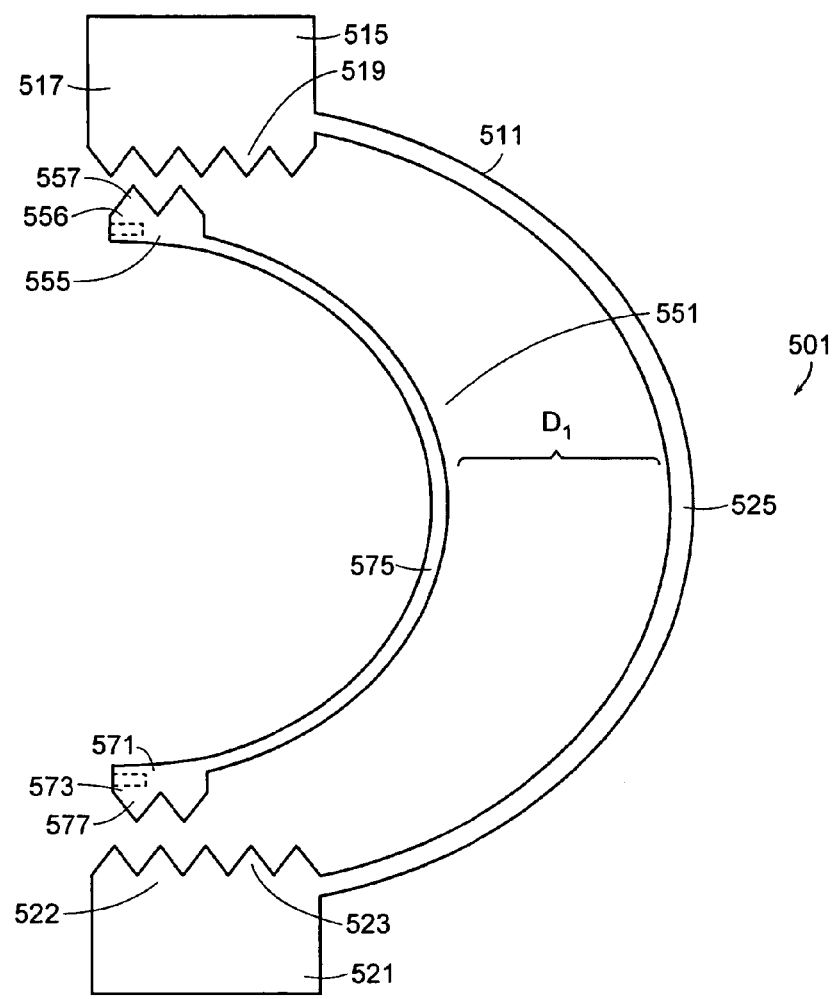
FIGS. 5a-b are side views of a fifth embodiment of the interspinous implant having outer and inner flexible shells.

In use, the implant of FIG. 5a is implanted into the interspinous void so that the opposing sets of teeth of the inner and outer shells are engaged to the opposed spinous processes, thereby providing a secure implant and defining a distance between the anterior walls $D_1$ of the inner and outer shells. If the clinician desires to change the stiffness of the implant, then the clinician may alter the distance D between the anterior walls of the inner and outer shells. Reducing the distance D between the anterior walls will cause a decrease in the stiffness of the implant, while increasing the distance D between the anterior walls will cause an increase in the stiffness of the implant.

Figure 5B:
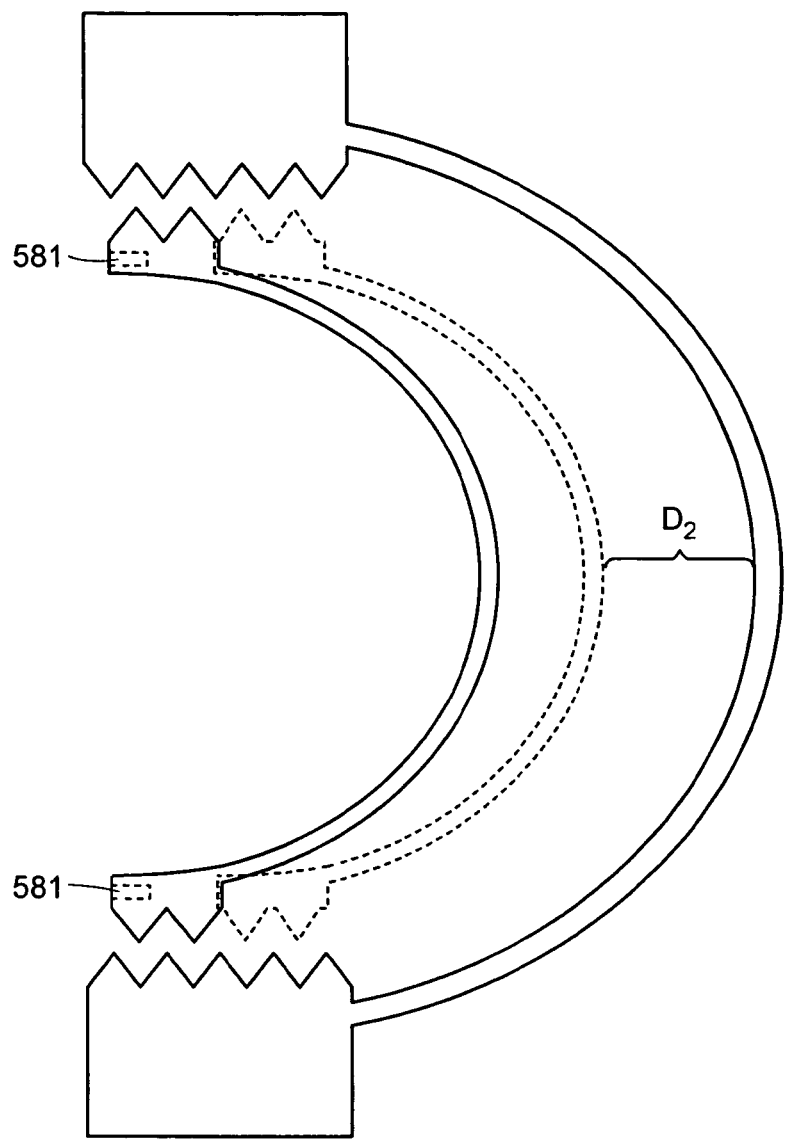

Now referring to FIG. 5b, when the clinician desires to decrease the stiffness of the implant of FIG. 5a, the clinician can use a pair of forceps (not shown) to engage the slots 581 provided on the upper and lower posterior portions of the inner shell. Providing a clamping force through the forceps squeezes together the posterior portions of the inner shell, thereby disengaging the respective pairs of teeth. The clinician can then move the disengaged inner shell anteriorly by a predetermined distance to a second position (shown in shadow), thereby decreasing the distance between the anterior walls to a smaller distance $D_2$ and lowering the stiffness of the implant.

In other embodiments, the slots of the implant of FIGS. 5a and 5b are replaced within other means for adjusting the distance D between the flexible anterior walls of the inner and outer shells. For example, in some embodiments, a set screw or a worm gear may be provided on the implant to alter the distance D, thereby adjusting the stiffness of the implant.

Therefore, in accordance with the present invention, there is provided an interspinous implant for insertion between adjacent spinous processes, the implant comprising:
   a) a flexible outer shell comprising:
   i) an upper posterior portion adapted to bear upon an upper spinous process and having a lower end having a first set of teeth,
   ii) a lower posterior portion adapted to bear upon a lower spinous process and having a upper end having a second set of teeth,
   iii) a flexible anterior wall connecting the upper and lower posterior portions of the flexible outer shell,
   b) a flexible inner shell comprising:
   i) an upper posterior portion having an upper end having a third set of teeth engaged in the first set of teeth,
   ii) a lower posterior portion having a lower end having fourth set of teeth engaged in the second set of teeth,
   iii) a flexible anterior wall connecting the upper and lower posterior portions.

In preferred embodiments, the implant of the present invention is used posteriorly in conjunction with a motion disc inserted within the disc space of the anterior portion of the spinal column. For example, in some embodiments, the implant of the present invention is used in conjunction with a motion disc having a large range of motion ("ROM"). Various motion discs are described by Stefee et al. in U.S. Pat. No. 5,071,437; Gill et al. in U.S. Pat. No. 6,113,637; Bryan et al. in U.S. Pat. No. 6,001,130; Hedman et al. in U.S.

Pat. No. 4,759,769; Ray in U.S. Pat. No. 5,527,312; Ray et al. in U.S. Pat. No. 5,824,093; Buttner-Janz in U.S. Pat. No. 5,401,269; and Serhan et al. in U.S. Pat. No. 5,824,094; all which documents are hereby incorporated herein by reference in their entireties. The flexibility of the flexible body provides resistance to extreme extension, thereby restricting the motion disc to a more narrow and more physiologically desirable range of motion.

Therefore, in accordance with the present invention, there is provided a kit for providing therapy to a functional spinal unit comprising an upper vertebrae having an upper spinous process, a lower vertebrae having a lower spinous process, and a disc space therebetween, the kit comprising:

a) an interspinous implant for insertion between adjacent spinous processes, the implant comprising a flexible (preferably, U-shaped) body comprising:
  i) an upper posterior portion having an upper surface adapted to bear upon an upper spinous process,
  ii) a lower posterior portion having a lower surface adapted to bear upon a lower spinous process, and
  iii) a flexible (preferably arcuate) anterior wall connecting the upper and lower portions, and
b) an artificial disc adapted for insertion into the disc space.

We claim:

1. An implant positionable between adjacent vertebrae, the implant comprising:
   an upper portion having a porous superior bone-contacting surface adapted to bear upon an upper vertebra and to promote bony ingrowth;
   first and second extensions projecting upwards from the superior surface and extending above the superior surface;
   a lower portion having a porous inferior bone-contacting surface adapted to bear upon a lower vertebra and to promote bony ingrowth;
   first and second extensions projecting downwards from the inferior surface and extending below the inferior surface; and
   a curved anterior wall connecting the upper and lower portions;
   wherein the implant is formed from titanium alloy, and
   wherein the implant is symmetrical about a transverse plane that extends through a midpoint of the curved anterior wall.

2. The implant of claim 1, wherein the upper and lower portions are substantially non-parallel.

3. The implant of claim 1, wherein the implant has a stiffness between 100 N/mm and 500 N/mm.

4. The implant of claim 1, wherein the superior and inferior porous surfaces each comprise a layer of small spherical particles or beads.

5. The implant of claim 1, further comprising an inner core disposed between the upper and lower portions.

6. The implant of claim 5, wherein a stiffness of the core is configured to increase post-operatively.

7. The implant of claim 1, further comprising metallic sidewalls extending between and formed integrally with the upper and lower portions.

8. The implant of claim 1, wherein the implant has a height between 10 mm and 20 mm, a length between 20 mm and 30 mm, and a width between 5 mm and 10 mm.

9. An implant for placement between adjacent vertebrae, the implant comprising:
   an upper portion having first and second upwardly-projecting extensions and a porous region disposed between the first and second extensions, the porous region being adapted to bear upon an upper vertebra and to promote bony ingrowth;
   a lower portion having first and second downwardly-projecting extensions and a porous region disposed between the first and second extensions, the porous region being adapted to bear upon a lower vertebra and to promote bony ingrowth; and
   a curved anterior surface extending between the upper and lower portions;
   wherein the implant is formed from titanium alloy, and
   wherein each of the first and second upwardly-projecting extensions and the first and second downwardly-projecting extensions has an end surface, said end surfaces lying in a common plane.

10. The implant of claim 9, wherein the upper and lower portions are substantially non-parallel.

11. The implant of claim 9, wherein the implant has a stiffness between 100 N/mm and 500 N/mm.

12. The implant of claim 9, wherein the porous regions each comprise a layer of small spherical particles or beads.

13. The implant of claim 9, further comprising an inner core disposed between the upper and lower portions.

14. The implant of claim 13, wherein a stiffness of the core is configured to increase post-operatively.

15. The implant of claim 9, further comprising metallic sidewalls extending between and formed integrally with the upper and lower portions.

16. The implant of claim 9, wherein the implant has a height between 10 mm and 20 mm, a length between 20 mm and 30 mm, and a width between 5 mm and 10 mm.

* * * * *